ROTARY DOUCHE FOR TREATING BREASTS

Original Filed April 17, 1970 3 Sheets-Sheet 1

ROTARY DOUCHE FOR TREATING BREASTS
Original Filed April 17, 1970 3 Sheets-Sheet 2
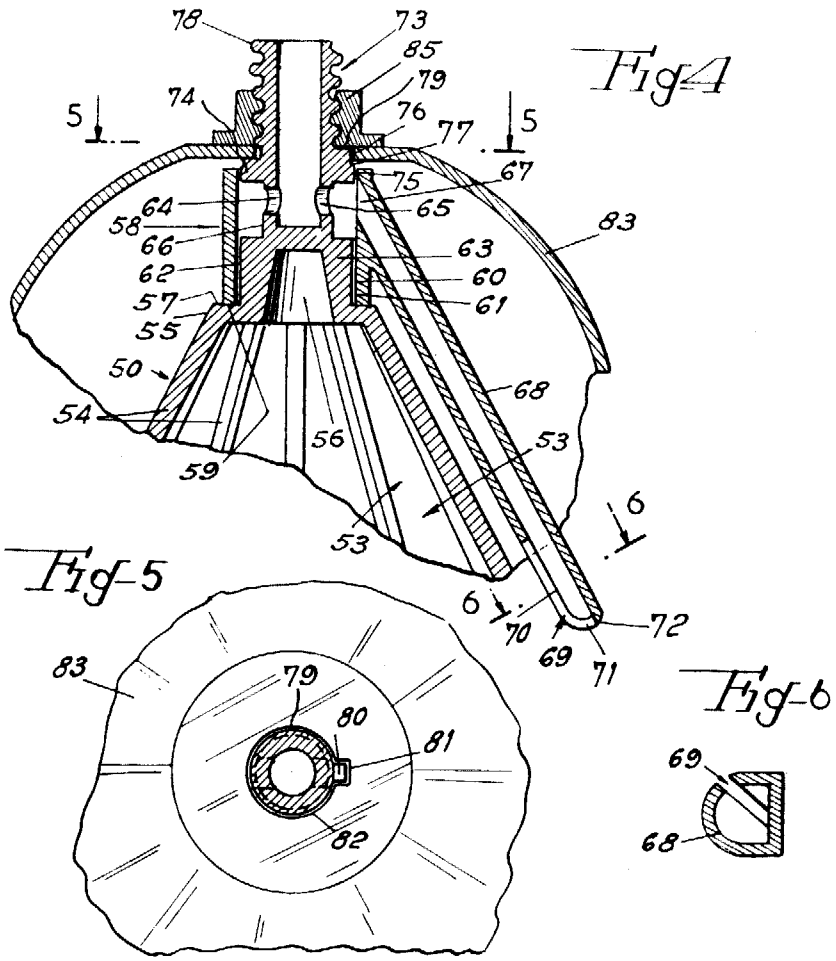
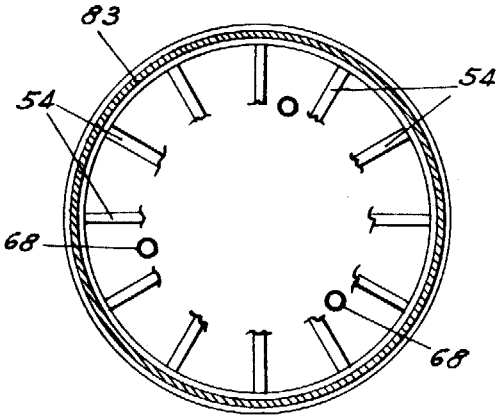

ROTARY DOUCHE FOR TREATING BREASTS

Original Filed April 17, 1970 3 Sheets-Sheet 3

United States Patent Office

Re. 28,023
Reissued May 28, 1974

28,023

ROTARY DOUCHE FOR TREATING BREASTS

Jacques Marcel Courtin, 35 Rue Tronchet,
75008 Paris, France

Original No. 3,667,455, dated June 6, 1972, Ser. No. 29,607, Apr. 17, 1970. Application for reissue Sept. 15, 1972, Ser. No. 289,217
Claims priority, application France, July 29, 1969, 6925877
Int. Cl. A61h *9/00*
U.S. Cl. 128—66 3 Claims

Matter enclosed in heavy brackets [ ] appears in the original patent but forms no part of this reissue specification; matter printed in italics indicates the additions made by reissue.

ABSTRACT OF THE DISCLOSURE

A rotary douche for treating breasts which is used with a water supply and which comprises three major component parts: a bell-shaped body, a stator and a rotor which are easily assembled and disassembled in order to facilitate the removal of deposits from the water supply such as calcium. The stator includes an extending lip for sealingly engaging the chest of the user. The stator is adapted to support the rotor for rotation thereon and includes a tubular portion extending through a portion of the bell-shaped body remote from the open end and adapted to be connected to a water supply. Ports are provided in the tubular member for conducting the water to the rotor. The rotor includes fingers having orifices at their tips so that the rotor is driven by reaction.

The invention relates to a rotary douche apparatus particularly for use in treating breasts, wherein rotary jets of water are provided by slots disposed at the tips of fingers forming part of a rotor. The jets of water so formed assure the rotation of the rotor by reaction.

The water for the douche is usually provided by directly connecting the apparatus to a water supply. Water, so provided, often contains calcium which causes encrustations and deposits to accumulate in the apparatus which at the end of a short period of time can interfere with the satisfactory operation of the apparatus.

Up until now, it has been necessary to proceed with relatively complicated measures in order to re-establish satisfactory operation. Such measures in practice necessitated the return of the apparatus to the place of manufacture.

An object of the present invention is to provide an apparatus of the above-described type which contrary to known devices of this type permits the user to easily remedy such an occurrence.

The invention is also intended to provide a rotor which is easy and economical to manufacture.

In achieving the above and other objects of the invention, there is provided an apparatus for treating breasts by rotary jets of water discharged from fingers fixed to a rotor supported for rotation on a stator including a lip for sealingly engaging the apparatus with the chest of a user and comprising a bell-shaped body for confining the jets of water within the body. The apparatus is characterized in that the three parts are mounted in a removable manner, a tubular coupling of the stator, which is provided for carrying water into the body, extending through a hole in the bell-shaped body disposed at the top of said body, and being threaded for securing the parts together in conjunction with a thumb-nut or the like.

The invention will be more fully understood from the description which follows with reference to the accompanying drawings, wherein:

FIG. 3 is a cross-section taken along line 3—3 in FIG. 1;

FIG. 4 is an enlarged fragmentary longitudinal section of the apparatus shown in FIG. 1;

FIG. 5 is a cross-section taken along line 5—5 in FIG. 4;

FIG. 6 is an enlarged cross-section of a finger taken along line 6—6 in FIG. 4;

Figure 2:
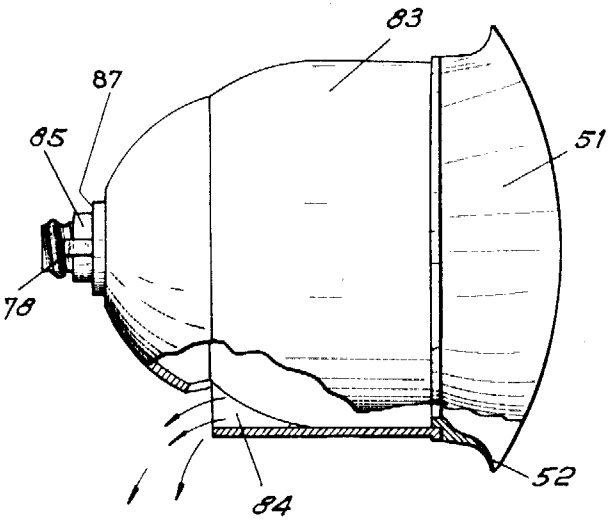
FIG. 2 is a lateral view of the apparatus shown in FIG. 1 rotated through 90° with a cutaway portion.
Figure 1:
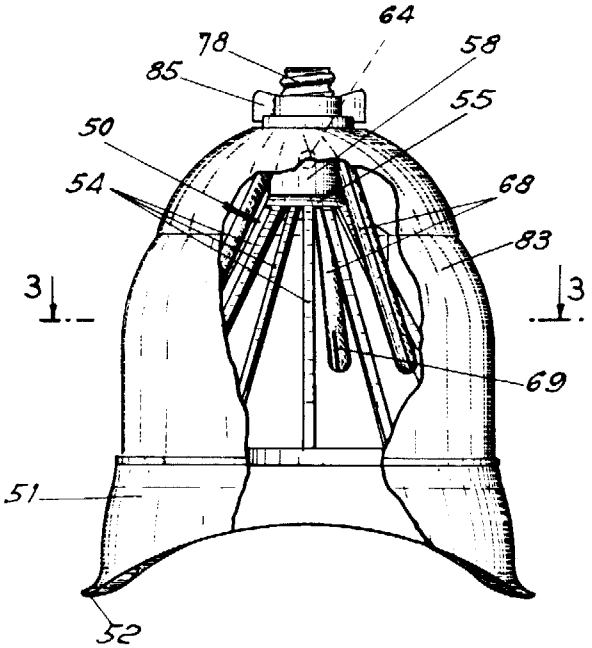
FIG. 1 is an elevation view with a cutaway portion of the apparatus according to the invention.
Figure 7:
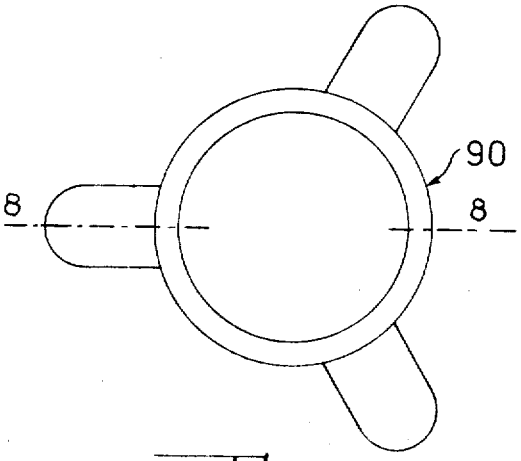
FIG. 7 is a plan view of a rotor according to another embodiment of the invention.
Figure 10:
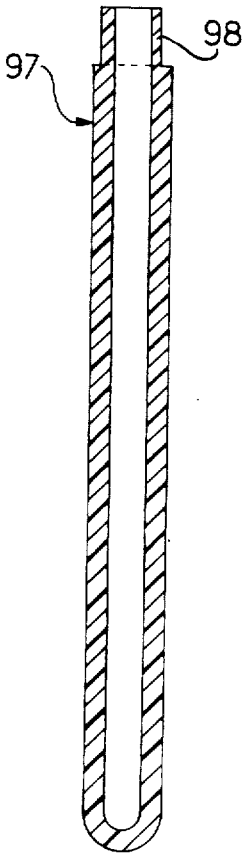
FIG. 10 is a longitudinal section of a spray finger.
Figure 8:
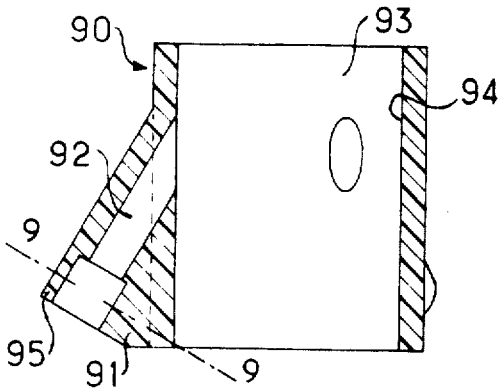
FIG. 8 is a longitudinal section taken along line 8—8 in FIG. 7.

The illustrated apparatus for treating breasts comprises a molded body 50 of plastic material comprising a flexible end portion 51 with a lip 52 adapted to sealingly engage against the chest, and a truncated conical sleeve 53 with ribs 54 which extend from the flange 55 which in turn extends from the stator 56. The stator 56 serves as a support for a rotor 58 by means of the annular shoulder 57 on the flange 55 which cooperates with edge 59 of the sleeve 60 of the rotor 58. The interior wall 61 of said sleeve 60 cooperates with the cylindrical exterior wall 62 of the bearing surface on the stator; this cooperation assures the guiding of the rotor during rotation. The water which also assures the rotation of the rotor is carried through two diametrically opposed ports or radial apertures 64 and 65 provided in the collar 66 of the stator. The hollow fingers or tubes 68 of the rotor are provided with internal bores and are integral with the sleeve 60, and inlet orifice 67 are provided therein and in sleeve 60 which are disposed at the same level as the said ports. The jets of water are effected by the slots 69 at the ends of the fingers 68 which are not disposed in diametrical planes and which comprise longitudinal portions 70 and portions 71 at the lower tips or distal ends 72 of the fingers.

According to the invention, the stator is extended by an end piece 73 which includes a flange 74 having an outer surface including a large diameter portion 75 and a small diameter portion 76 with an annular shoulder 77 therebetween, and a threaded tubular coupling 78 extending from the flange 74.

The combination consisting of the end piece 73, the stator 56, the truncated conical sleeve 53 and the end portion 51 is formed as a single piece which can be molded of plastic material.

A detent 80 projects from the annular surface 79 which conencts the flange 74 to the threaded coupling 78. The detent cooperates with a notch 81 in mating engagement. A second molded body 83 formed as a bell is provided with an aperture through which passes the tubular coupling 78. A precise angular positioning of the molded body 50 relative to the bell-shaped body 83 can be effected by means of the detent and notch. An outlet orifice 84 is provided in the bell-shaped body for discharging the water and is located in the lower surface of the body when it is in position on the chest. The bell-shaped body 83 is also molded of plastic material and is preferably transparent.

The thumb-nut 85 is tightened on the threaded portion of the coupling 78 until the lower face 86 is in engagement with the flat portion 87 on the bell-shaped body 83 which extends about the cutout 82 and assures the joining of the bell-shaped body 83 with the molded body 50.

If, for example, owing to a build-up of deposits, the flow of water is not adequate or the rotation of the rotor is impeded thereby, it is possible to disassemble the apparatus, separate it into its three component parts, clean, or possibly replace the rotor with a new rotor. Upon reassembly, satisfactory operating conditions are immediately re-established.

Figure 9:
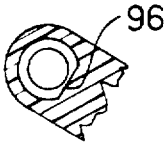
FIG. 9 is a sectional view taken along line 9—9 in FIG. 8.
Figure 11:
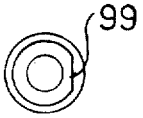
FIG. 11 is a top plan view of the spray finger in FIG. 10.

Reference is next made to FIGS. 7–11, which relate to a rotor which can easily be formed by molding and whose guiding surface for engagement with the stator is perfectly smooth without any machining being necessary. According to the illustrated embodiment of the invention, the rotor is manufactured in several parts, i.e. a central portion or sleeve and the spray fingers. The sleeve 90 (FIGS. 7 and 8) is generally cylindrical in shape and includes projecting portions 91, three of which are shown in this embodiment. These projections are hollow and include conduits 92 which communicate with the central conduit 93. Such a sleeve can be easily formed by molding in a single operation so that there is no joint in said sleeve and it is therefore not necessary to remove burrs from the interior surface 94 thereof. Connecting sockets 95 are provided at the end of the conduits 92 and include flats 96 (FIG. 9).

The fingers 97 (FIGS. 10 and 11) include connecting collars 98 having flats 99 which assure a suitable orientation of the fingers 97 relative to the projecting portions 91.

The slots at the end of the fingers 97 are obliquely arranged therein in order to assure the rotation of the rotor, the propelling jet simultaneously assuring the massage of the breasts.

The fingers 97 are assembled in the projections 91 by simply inserting the connecting collars 98 into the sockets 95 and by cementing, gluing or the like.

What I claim is:

1. A breast hydro massaging device comprising a bell-shaped housing including an apex and a lateral wall providing a mouth and being provided with an opening in said apex and an outlet orifice in said lateral wall; a one-piece stator including a nipple having a closed inner end and provided with radial apertures and extending through said opening, bars integral with said nipple and forming a cone-shaped cage, and a flexible lip [on said bars and] extending through the mouth of the housing and adapted to sealingly engage the chest of a user; a sleeve, water discharging tubes provided with slots at the distal ends thereof and integral with said sleeve, said sleeve being rotatively mounted on said nipple inside the housing, said nipple having a threaded portion, and a nut threadably engaged with said threaded portion of said nipple outside the housing.

2. A device as claimed in claim 1 wherein said opening is provided with a notch on its contour, said nipple in- are hollow and provided with internal bores, said sleeve cluding a detent adapted to cooperate with said notch to locate said housing.

3. A device as claimed in claim 2 wherein said tubes being provided with openings communicating with said bores and adapted for alignment with said radial apertures.

References Cited

The following references, cited by the Examiner, are of record in the patented file of this patent or the original patent.

UNITED STATES PATENTS

| | | | |
|---|---|---|---|
| 2,699,773 | 1/1955 | Nemeth | 128—66 |
| 1,025,236 | 5/1912 | Behm | 128—66 |

FOREIGN PATENTS

| | | | |
|---|---|---|---|
| 1,014,584 | 6/1952 | France | 128—66 |

LAWRENCE W. TRAPP, Primary Examiner